United States Patent [19]

Van der Knaap

[11] Patent Number: Plant 6,868

[45] Date of Patent: Jun. 20, 1989

[54] CHRYSANTHEMUM PLANT NAMED PINK MONEYMAKER

[75] Inventor: Jacques C. M. Van der Knaap, De Lier, Netherlands

[73] Assignee: Fides Beheer B.V., De Lier, Netherlands

[21] Appl. No.: 124,548

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A chrysanthemum plant named Pink Moneymaker, particularly characterized by its anemone capitulum type and flat capitulum form; medium pink ray floret color, and by its medium pink mature petaloids which form around the disc florets.

1 Drawing Sheet

The present invention comprises a new and distinct cultivar of Chrysanthemum, botanically known as *Chrysanthemum morifolium*, and referred to by the cultivar name Pink Moneymaker.

Pink Moneymaker is a spontaneous mutation of Moneymaker, disclosed in a pending application of applicant. Pink Moneymaker was discovered by applicant in 1985 in De Lier, The Netherlands while growing in a cultivated bed of the parent cultivar Moneymaker. The new cultivar was immediately recognized due to its medium pink ray floret color, as compared with the light peach-pink ray floret color of Moneymaker.

The first act of asexual reproduction of Pink Moneymaker was accomplished when vegetative cuttings were taken following discovery in a controlled environment in De Lier, The Netherlands by a technician working under formulations established and supervised by applidant. Horticultural examination of selected units has demonstrated that the combination of characteristics as herein disclosed for Pink Moneymaker are firmly fixed and are retained through successive generations of asexual reproduction.

Pink Moneymaker has not been observed under all possible environmental conditions. The phenotype may vary significantly with variations in environment such as temperature, light intensity, and day length. The following observations, measurements and comparisons describe plants grown in De Lier, The Netherlands under geeenhouse conditions which approximate those generally used in commercial practice.

The following traits have been repeatedly observed and are determined to be basic characteristics of Pink Moneymaker, which in combination distinguish this Chrysanthemum as a new and distinct cultivar:

1. Flat capitulum form.
2. Anemone capitulum type.
3. Medium pink ray floret color.
4. Diameter across the face of the capitulum is 40–45 mm, approximately 0.5 cm smaller than the parent cultivar, Moneymaker.
5. Petaloids are formed around the disc florets, which are at their outer periphery similar in color to the ray florets, merging into disc florets in the center, which are similar in color.

Pink Moneymaker is similar in most respects to its parent Moneymaker, differing therefrom in ray floret color and flower size. Pink Moneymaker is also similar except for color to Apricot Moneymaker and Lilac Moneymaker, both color mutations of Moneymaker and disclosed in pending applications of applicant. Of the mutations noted, Pink Moneymaker has the smallest diameter inflorescence, and also 3–4 days later response.

The accompanying photographic drawing shows in front view typical inflorescence and foliage characteristics of Pink Moneymaker, with colors being as true as possible with illustrations of this type.

In the following description, color references are made to The Royal Horticultural Society Colour Chart. The color values were determined between 11:00 a.m. and 12:00 noon in September under natural daylight at De Lier, The Netherlands.

Classification:

*Botanical.*—*Chrysanthemum morifolium*, Ramat., cv. Pink Moneymaker.

*Commercial.*—Cut anemone spray.

INFLORESCENCE

A. Capitulum:

*Form.*—Flat.

*Type.*—Anemone.

*Diameter across face.*—40–45 mm.

B. Corolla of ray florets:

*Color (general tonality from a distance of three meters).*—Medium pink.

*Color (upper surface).*—36B-C to 65D, with center approximately 68D.

*Color (under surface).*—Somewhat lighter than 36B-C.

C. Corolla of disc florets:

*Color.*—Green 145A-B (immature) maturing close to color (36B-C) of ray florets; petaloids around disc florets are generally the same color as the ray florets, particularly at the juncture of the petaloids and ray florets.

D. Reproductive organs:

*Androecium.*—Present only in disc florets; numerous.

*Gynoecium.*—Present in both disc and ray florets; numerous.

PLANT

A. General appearance:

*Height.*—90 cm.

B. Foliage:

*Color* (*upper surface*).—137A.

*Color* (*under surface*).—137B.

*Shape.*—Deeply serrated.

I claim:

1. A new and distinct cultivar of Chrysanthemum plant named Pink Moneymaker, as described and illustrated, and parts thereof.

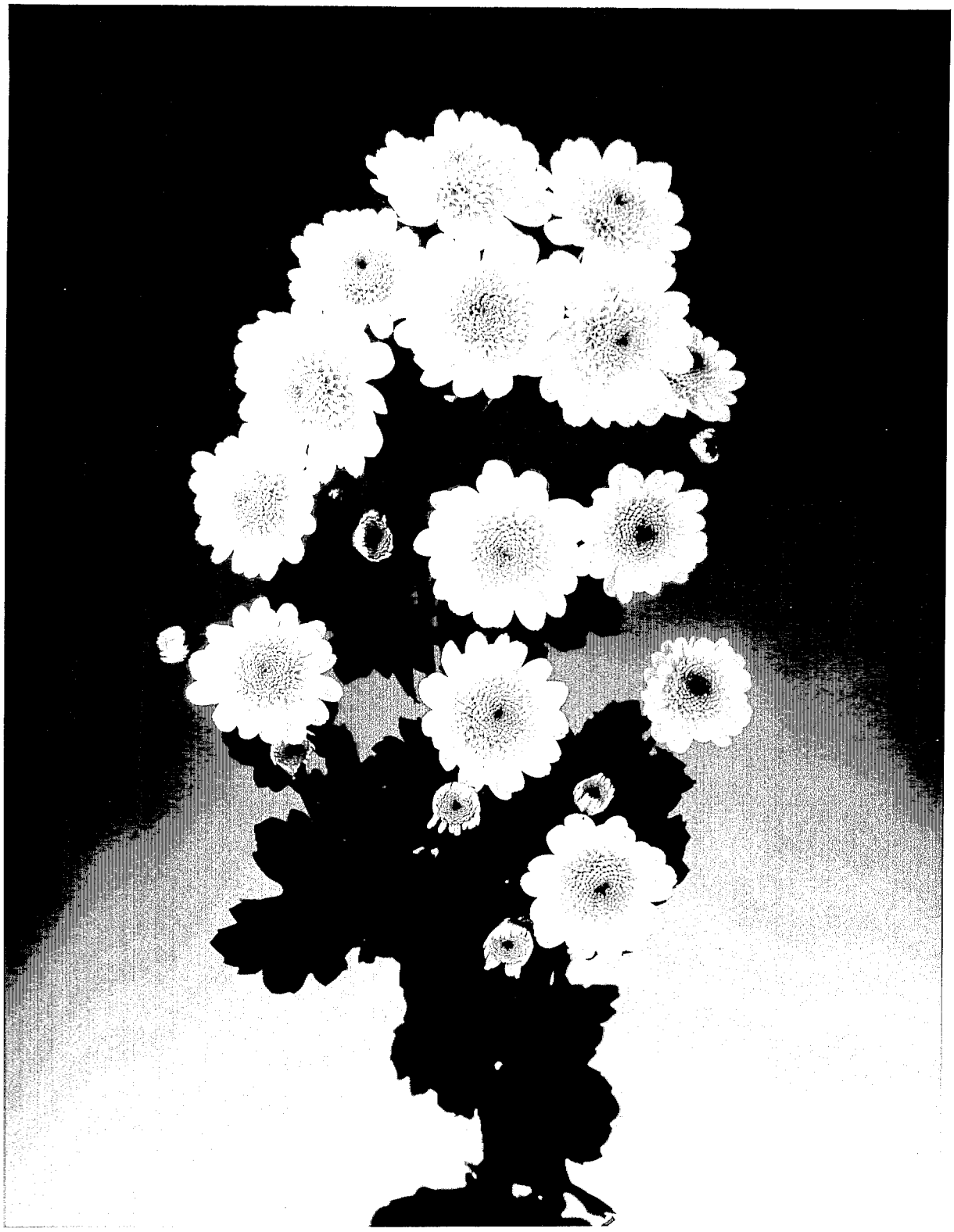

* * * * *